United States Patent
Wenzel et al.

(10) Patent No.: US 9,238,145 B2
(45) Date of Patent: Jan. 19, 2016

(54) LEADLESS IMPLANTABLE DEVICE DELIVERY APPARATUS

(71) Applicant: BIOTRONIK SE & Co. KG, Berlin (DE)

(72) Inventors: Matthias Wenzel, Berlin (DE); Michael J. Ayton, Beaverton, OR (US); Karl Nordstrom, Woodburn, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 106 days.

(21) Appl. No.: 14/035,824

(22) Filed: Sep. 24, 2013

(65) Prior Publication Data
US 2014/0148815 A1  May 29, 2014

Related U.S. Application Data

(60) Provisional application No. 61/730,058, filed on Nov. 27, 2012.

(51) Int. Cl.
| | | |
|---|---|---|
| *A61B 19/00* | (2006.01) | |
| *A61B 17/34* | (2006.01) | |
| *A61N 1/375* | (2006.01) | |
| *A61N 1/00* | (2006.01) | |

(52) U.S. Cl.
CPC .......... *A61N 1/3756* (2013.01); *A61B 17/3468* (2013.01)

(58) Field of Classification Search
CPC ..... A61N 1/056; A61N 1/0565; A61N 1/057; A61N 2001/058; A61N 1/059; A61N 1/3756; A61F 2/2427; A61M 25/0043; A61M 2025/09141; F16D 25/00; A61B 19/201; A61B 17/203; A61B 17/3468; A61B 18/201; A61B 2001/058; A61B 2001/0578

USPC .......... 606/129; 600/433–435, 585, 373–375; 607/36, 119, 126–127, 12, 130, 131
See application file for complete search history.

(56) References Cited

U.S. PATENT DOCUMENTS

| | | | |
|---|---|---|---|
| 2008/0051851 A1 | 2/2008 | Lin | |
| 2009/0099554 A1* | 4/2009 | Forster et al. | 606/1 |
| 2009/0163780 A1* | 6/2009 | Tieu | 600/301 |
| 2012/0172690 A1* | 7/2012 | Anderson et al. | 600/347 |

FOREIGN PATENT DOCUMENTS

| | | |
|---|---|---|
| WO | 2004/064729 | 8/2004 |
| WO | 2005/007237 | 1/2005 |

OTHER PUBLICATIONS

European Search Report, dated Jan. 14, 2014, 5 pages.

* cited by examiner

*Primary Examiner* — Katrina Stransky
*Assistant Examiner* — Katherine Schwiker
(74) *Attorney, Agent, or Firm* — ARC IP Law, PC; Joseph J. Mayo

(57) ABSTRACT

A leadless implantable device delivery apparatus that enables testing of an implantation site before permanent implantation and enables secure attachment at the site while minimizing effects of the implantation procedure. Embodiments include a delivery sheath configured to accommodate a leadless implantable device, the leadless implantable device having an anchor that includes at least one projection configured to physically attach the anchor to tissue, such as heart tissue. In addition, embodiments include an adapter that resides within the delivery sheath and is configured to impart rotational force at the distal end of the adapter that is applied to the proximal end of the adapter to rotate the anchor associated with the implantable device.

8 Claims, 4 Drawing Sheets

LEADLESS IMPLANTABLE DEVICE DELIVERY APPARATUS

This application claims the benefit of U.S. Provisional Patent Application 61/730,058, filed on 27 Nov. 2012, the specification of which is hereby incorporated herein by reference.

BACKGROUND OF THE INVENTION

1. Field of the Invention

At least one embodiment of the invention generally relates to an apparatus for implantation of medical devices and more particularly, but not by way of limitation, relates to a leadless implantable device delivery apparatus.

2. Description of the Related Art

Implantable medical devices may be implanted in patients in need of cardiac monitoring and if necessary, electrical stimulation. Leadless implantable devices, such as a leadless pacemaker for example have been developed to eliminate problems associated with electrode leads, which are prone to failure over time. In addition, explantation of electrode leads that have been implanted for long periods of time increases the risk of complications. Electrical energy is sensed via the implantable device and analyzed locally or with an associated implantable medical device, or external device through wireless communications for example. Therapeutic energy is provided by the implantable device, for example in a heart to ensure that the heart provides life-sustaining contractions that pump blood through the patient's body. Generally, the leadless implantable devices are physically attached to the heart in a manner that is intended to be relatively permanent, so as to ensure long term robust electrical contact with the specific heart tissue and in addition to avoid disengagement, which may lead to problems in the lungs if the leadless implantable device detaches from the tissue. Typical leadless implantable devices provide attachment mechanisms such as screws or tines that project in one way or another into the tissue of the heart.

Implantation of leadless implantable devices may be performed in a variety of ways, for example via the femoral vein. Advantages of this type of implantation include minimization of infection and reduction in the amount of X-rays in the implantation process. In addition, this type of implantation minimizes the surgical procedures involved, for example since no surgical pocket is required to house an implantable device with leads that extend to the heart. This type of implantation also minimizes the amount of time that a patient must remain in the hospital. However, the disadvantages are that the leadless implantable devices currently implanted are difficult to position at an optimal implantation site, and once implanted, generally with hooks, these types of devices are generally abandoned when their battery life is exhausted since their implantation is intended to be permanent.

BRIEF SUMMARY OF THE INVENTION

At least one embodiment of the invention provides a leadless implantable device delivery apparatus that for example enables testing of an implantation site before permanent implantation and enables secure attachment of a leadless implantable device at the site while minimizing effects of the implantation procedure.

Embodiments of the invention generally include a delivery sheath that generally encloses an adapter. The delivery sheath may accommodate, house or otherwise couple with the leadless implantable device. The leadless implantable device includes or is otherwise coupled with an anchor having at least one projection that may physically attach the anchor to tissue, for example heart tissue. The adapter is capable of imparting rotational force at the distal end of the adapter that is applied to the proximal end of the adapter to rotate the leadless implantable device and/or anchor coupled therewith.

Embodiments of the adapter may include a press-fit coupling element at the proximal end that may press against a side of the adapter to enable the adapter to rotate when the rotational force is applied. This provides sufficient torque to implant a rotational type anchor.

With respect to the implantable device, embodiments of the adapter may include a force-fit coupling element at the distal end to couple with a side of the implantable device to enable the implantable device to rotate when the rotational force is applied. Embodiments of the force-fit coupling element at the distal end may couple with a side of the implantable device to enable the implantable device to disengage from the adapter when an opposing rotational force with respect to the rotational force is applied. In one or more embodiments, the force-fit element may include at least one pin, wherein the implantable device includes at least one indentation coupled with the pin to enable the adapter to impart the rotational force to rotate the implantable device via the pin. Any other force-fit element and corresponding device on the implantable device may be utilized in keeping with the spirit of the invention, as one skilled in the art will recognize.

During delivery of the leadless implantable device, rotation in one direction imparts rotational force onto the anchor element coupled with the implantable device, wherein the rotational force is transmitted from the press-fit coupling element to the proximal portion of the adapter to the distal portion of the adapter to the implantable device to the anchor. During release, the press-fit coupling element is disengaged from a corresponding cavity in the delivery sheath, which disables rotational forces from travelling through or otherwise along the adapter, and which ensures that no disengagement of the anchor occurs when the adapter is uncoupled from the implantable device.

Other embodiments of the adapter may utilize a faceted head, for example a hex nut or any other shape that allows rotational forces to be applied to the leadless implantable device. Generally, the implantable device includes a corresponding faceted element to enable the adapter to impart the rotational force to rotate the implantable device via the faceted head. One or more embodiments of the adapter may include a seal wherein the adapter includes a hollow portion for example in the center portion of the faceted head, wherein the faceted head may disengage from the implantable device when the hollow portion of the adapter is filled with liquid introduced between the faceted element and faceted head. In one or more embodiments, the press-fit coupling element at the proximal end is disengaged as the adapter is filled with liquid so that the press-fit coupling element no longer presses against the side of the adapter. This disables rotational forces from rotating the distal end of the adapter.

Other embodiments of the adapter may utilize a ball and ramp at the distal end coupled with at least one wire within the adapter, wherein the at least one wire may enable the adapter to rotate when the rotational force is applied to the at least one wire near the proximal end of the adapter. In one embodiment a helix or double helix may be utilized as the at least one wire to provide the rotational force within the adapter. Any mechanism at the proximal side of the adapter may be utilized to impart the rotational force including manual or automated mechanisms for example. In one or more embodiments, the implantable device includes a corresponding rotational element to enable the adapter to impart the rotational force to rotate the implantable device via the ball and ramp. In one or more embodiments, the ball and ramp may disengage the adapter from the implantable device when longitudinal force is applied in a direction away from the implantable device, for example when enough force is applied to overcome the lateral force applied by the ball to a corresponding element on the implantable device.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
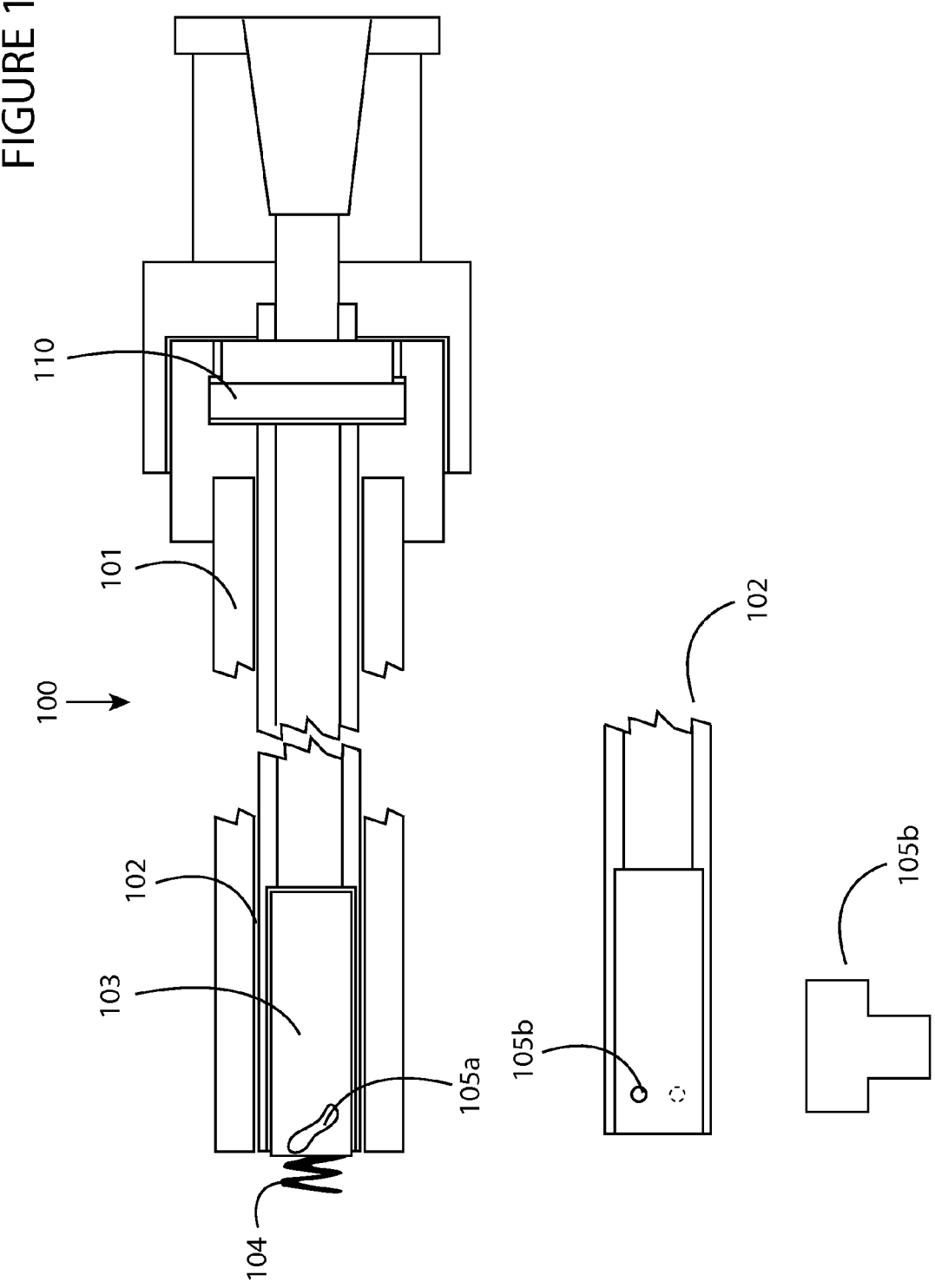
FIG. 1 shows a side view of a first embodiment of the invention, along with a view of the distal end of the adapter and a first embodiment of a force-fit element.

FIG. 1 shows a side view of a first embodiment of the leadless implantable device delivery apparatus 100, along with a view of the distal end of the adapter 102 below apparatus 100 and a side view of a first embodiment of force-fit element 105b shown below adapter 102, wherein the force-fit element is configured to couple with the side of implantable device 103, for example via force-fit groove 105a. Embodiments of the invention generally include delivery sheath 101, shown as a distal portion on the left and proximal portion on the right wherein the broken lines show an arbitrary length of a single delivery sheath. Embodiments of delivery sheath 101 may accommodate leadless implantable device 103 having anchor 104 that includes at least one projection that may physically attach the anchor to tissue, for example heart tissue. In addition, embodiments of the invention utilize adapter 102 having a distal end and a proximal end, shown on the left and right respectively, wherein the adapter may reside within delivery sheath 101 and wherein the adapter may impart rotational force at the distal end of the adapter that is applied to the proximal end of the adapter 102 to rotate implantable device 103.

Embodiments of the adapter may include press-fit coupling element 110 at the proximal end that may press against a side of the adapter to enable the adapter to rotate when the rotational force is applied. This provides sufficient torque to implant a rotational type anchor. From the viewpoint of the implantable device, embodiments of the adapter may include force-fit coupling element 105b at the distal end that may couple with a side of the implantable device to enable the implantable device to rotate when the rotational force is applied. Embodiments of the force-fit coupling element at the distal end may couple with a side of said implantable device to enable the implantable device to disengage from the adapter when an opposing rotational force with respect to the rotational force is applied.

In one or more embodiments, the force-fit element may include at least one pin 105b, wherein the implantable device includes at least one indentation 105a that may couple with the pin to enable the adapter to impart the rotational force to rotate the implantable device 103 via the pin. Any other force-fit element and corresponding device on the implantable device may be utilized in keeping with the spirit of the invention, as one skilled in the art will recognize.

Figure 2:
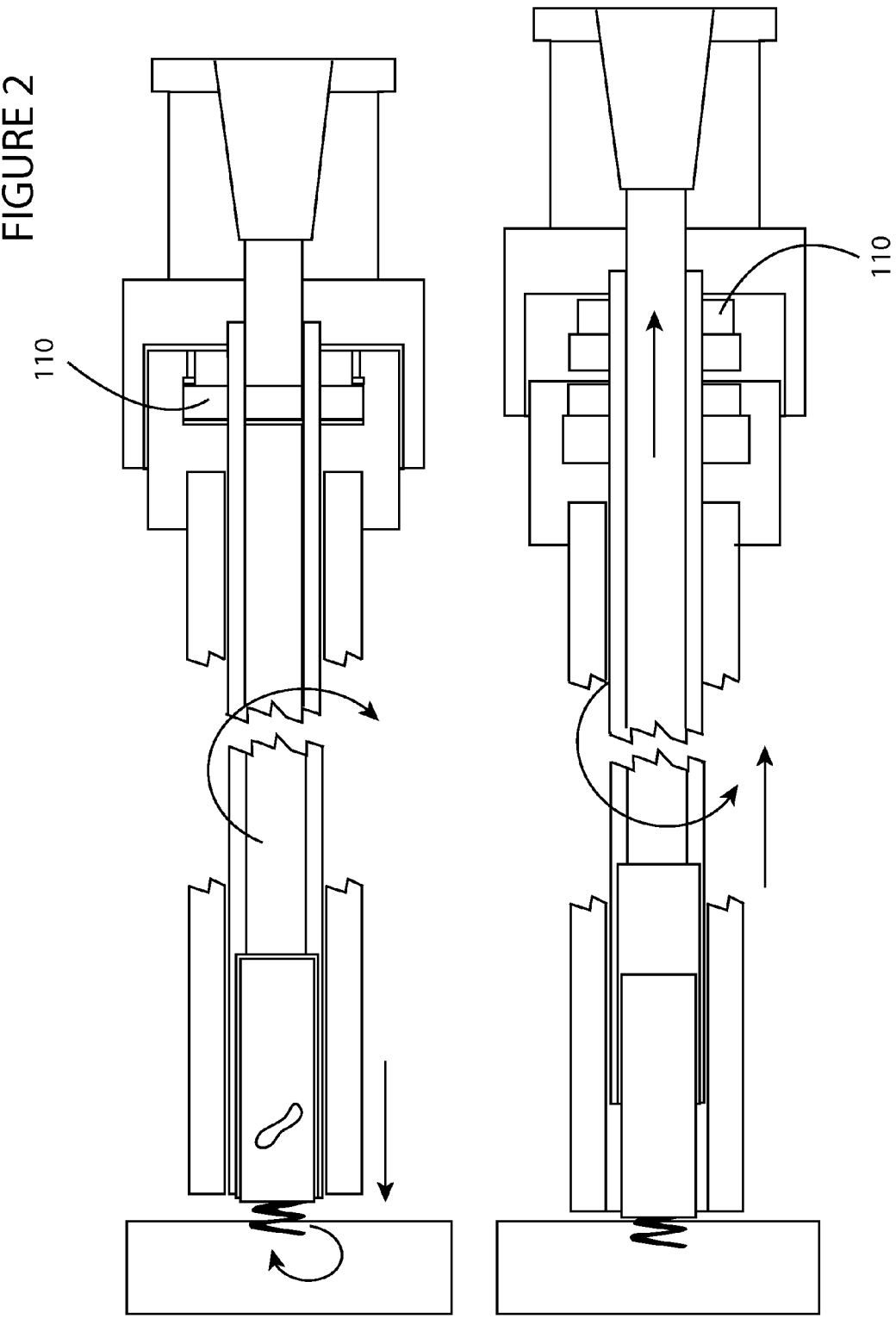
FIG. 2 shows a side view of the first embodiment of the invention shown in FIG. 1 during delivery of an implantable medical device and during release of the implantable medical device.

FIG. 2 shows a side view of the first embodiment of the invention shown in FIG. 1 during delivery of an implantable medical device and during release of the implantable medical device. During delivery, rotation in one direction imparts rotational force onto the anchor element coupled with the implantable device, wherein the rotational force is transmitted from press-fit coupling element 110 to the proximal portion of the adapter to the distal portion of the adapter to the implantable device to the anchor as is shown in the top portion of the figure. During release, press-fit coupling element 110 is disengaged from a corresponding cavity in the delivery sheath shown just to the left of press-fit coupling element 110 in the lower figure, which disengages rotational forces from travelling through the adapter, and which ensures that no disengagement of the anchor occurs when the adapter is uncoupled with the implantable device.

Figure 3:
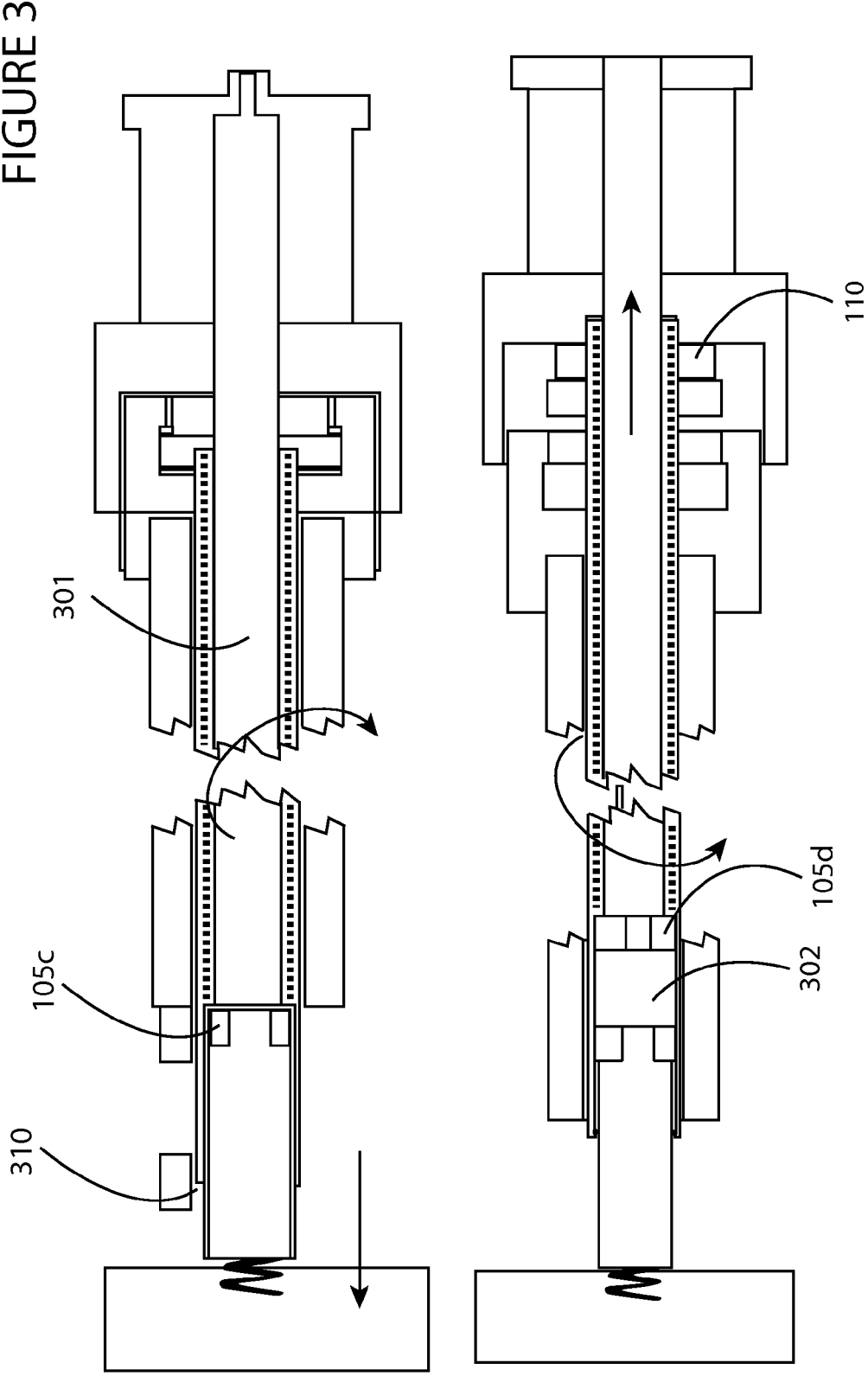
FIG. 3 shows a side view of a second embodiment of the invention during delivery of an implantable medical device and during release of the implantable medical device.

FIG. 3 shows a side view of a second embodiment of the invention during delivery of an implantable medical device and during release of the implantable medical device. This embodiment of the adapter may utilize faceted head 105d wherein the implantable device includes a corresponding faceted element 105c to enable the adapter to impart the rotational force to rotate the implantable device via the faceted head. One or more embodiments of the adapter may include seal 310 wherein the adapter includes a hollow portion for example in the center portion of faceted head 105d, wherein the faceted head may disengage from the implantable device when the hollow portion of the adapter is filled with liquid 301 introduced between faceted element 105c and faceted head 105d, for example in location 302. In one or more embodiments, press-fit coupling element 110 at the proximal end is disengaged as the adapter is filled with liquid in location 302 so that the press-fit coupling element no longer presses against the side of the adapter. This disables rotational forces from rotating the distal end of the adapter. In one or more embodiments, liquid 301 may be of a temperature that alters the physical properties of the force-fit or rotational elements which may be may of temperature dependent materials such as nitinol for example, so that the adapter either disengages the leadless device or disables rotation of the leadless device or both.

Figure 4:
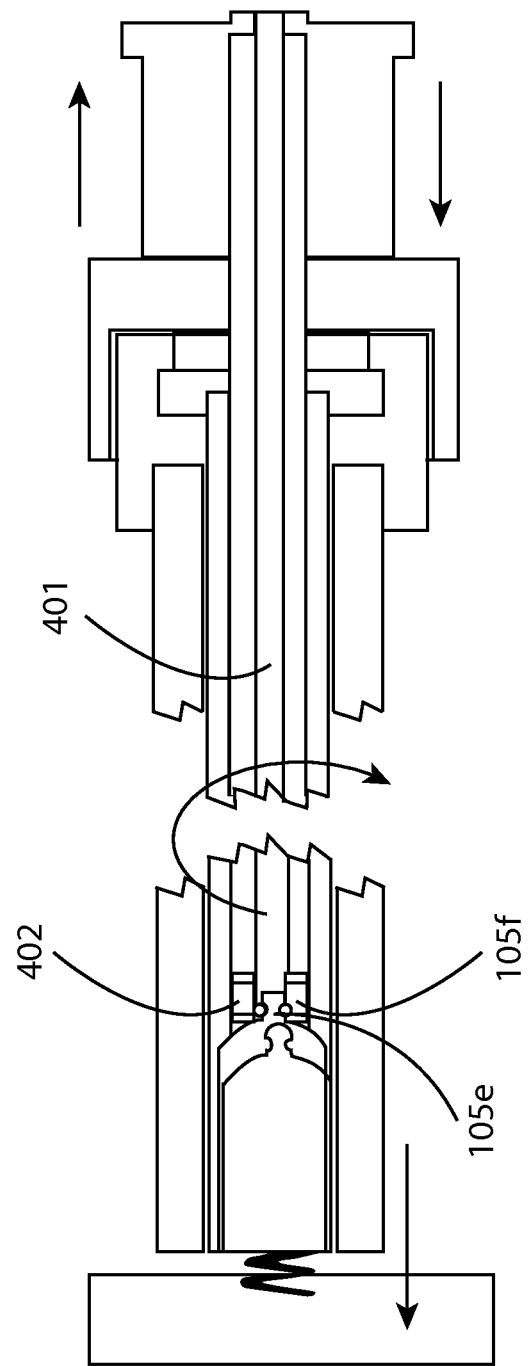
FIG. 4 shows a side view of a third embodiment of the invention.

FIG. 4 shows a side view of a third embodiment of the invention having an adapter that includes ball and ramp 105f at the distal end 402 coupled with at least one wire 401 within the adapter wherein the at least one wire may enable the adapter to rotate when the rotational force is applied to the at least one wire near the proximal end of the adapter. In one embodiment a helix or double helix may be utilized as the at least one wire 401 to provide the rotational force within the adapter. Any mechanism at the proximal side of the adapter may be utilized to impart the rotational force including manual or automated mechanisms for example. In one or more embodiments, the implantable device includes a corresponding rotational element 105e to enable the adapter to impart the rotational force to rotate the implantable device via the ball and ramp. In one or more embodiments, the ball and ramp may disengage the adapter from the implantable device when longitudinal force is applied in a direction away from the implantable device, for example when enough force is applied to overcome the lateral force applied by the ball to a corresponding element on the implantable device.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A leadless implantable device delivery apparatus comprising:
   a leadless implantable device having an anchor;
   a delivery sheath configured to accommodate the leadless implantable device, wherein said anchor comprises at least one projection configured to physically attach said anchor to tissue;
   an adapter comprising a proximal end and a distal end, wherein said adapter is configured to reside within said delivery sheath and to impart rotational force at said distal end of said adapter that is applied to said proximal end of said adapter to rotate said implantable device;
   wherein said adapter further comprises a faceted head, a seal and a hollow portion,
   wherein said implantable device comprises a corresponding faceted element to enable said adapter to impart said rotational force to rotate said implantable device said faceted head, and,
   wherein said facected head is configured to disengage said implantable device when said hollow portion of said adapter is filled with liquid.

2. The leadless implantable device delivery apparatus according to claim 1,
   wherein
   said adapter further comprises a press-fit coupling element at said proximal end configured to press against a side of said adapter to enable said adapter to rotate when said rotational force is applied.

3. The leadless implantable device delivery apparatus according to claim 1,
   wherein
   said adapter further comprises a force-fit coupling element at said distal end configured to couple
   with a side of said implantable device to enable said implantable device to rotate when said rotational force is applied.

4. The leadless implantable device delivery apparatus according to claim 1,
   wherein
   said adapter further comprises a force-fit coupling element at said distal end configured to couple with a side of said implantable device to enable said implantable device to disengage from said adapter when an opposing rotational force with respect to said rotational force is applied.

5. The leadless implantable device delivery apparatus according to claim 1,
   wherein
   said adapter further comprises a temperature dependent force-fit coupling element at said distal end configured to couple with a side of said implantable device to enable said implantable device to disengage from said adapter when a temperature is applied that alters a physical property of said temperature dependent force-fit coupling element.

6. The leadless implantable device delivery apparatus according to claim 2,
   wherein
   said press-fit coupling element at said proximal end is configured to disengage as said adapter is filled with liquid such that said press-fit coupling element no longer presses against said side of said adapter to disable said rotational force to rotate a distal end of said adapter.

7. A leadless implantable device delivery apparatus comprising:
   a leadless implantable device having an anchor;
   a delivery sheath configured to accommodate the leadless implantable device, wherein said anchor comprises at least one projection configured to physically attach said anchor to tissue;
   an adapter comprising a proximal end and a distal end, wherein said adapter is configured to reside within said delivery sheath and to impart rotational force at said distal end of said adapter that is applied to said proximal end of said adapter to rotate said implantable device;
   wherein said adapter further comprises
     a press-fit coupling element at said proximal end configured to press against a side of said adapter to enable said adapter to rotate when said rotational force is applied;
     a force-fit coupling element at said distal end configured to couple with a side of said implantable device to enable said implantable device to rotate when said rotational force is applied;
     wherein said force-fit coupling element is further configured to couple with said side of said implantable device to enable said implantable device to disengage from said adapter when an opposing rotational force with respect to said rotational force is applied;
     a faceted head; and,
     a seal and a hollow portion
     wherein said implantable device comprises a corresponding faceted element to enable said adapter to impart said rotational force to rotate said implantable device via said faceted head,
     wherein said faceted head is configured to disengage said implantable when said hollow portion of said adapter is filled with liquid; and,
     wherein said press-fit coupling element at said proximal end is configured to disengage as said adapter is filled with said liquid such that said press-fit coupling element no longer presses against said side of said adapter to disable said rotational force to rotate a distal end of said adapter.

8. A leadless implantable device delivery apparatus comprising:
   a leadless implantable device having an anchor;
   a delivery sheath configured to accommodate the leadless implantable device, wherein said anchor comprises at least one projection configured to physically attach said anchor to tissue; and,
   an adapter comprising a proximal end and a distal end, wherein said adapter is configured to reside within said delivery sheath and to impart rotational force at said distal end of said adapter that is applied to said proximal end of said adapter to rotate said implantable device;
   wherein said adapter further comprises a press-fit coupling element at said proximal end configured to press against a side of said adapter to enable said adapter to rotate when said rotational force is applied, and wherein said press-fit coupling element at said proximal end is configured to disengage as said adapter is filled with liquid such that said press-fit coupling element no longer presses against said side of said adapter to disable said rotational force to rotate a distal end of said adapter.

* * * * *